(12) United States Patent
Obszanski

(10) Patent No.: US 12,324,625 B2
(45) Date of Patent: Jun. 10, 2025

(54) OPHTHALMIC DEVICE

(71) Applicant: Aston Vision Sciences Ltd., Birmingham (GB)

(72) Inventor: Karl Obszanski, Birmingham (GB)

(73) Assignee: Aston Vision Sciences Ltd., Birmingham (GB)

( * ) Notice: Subject to any disclaimer, the term of this patent is extended or adjusted under 35 U.S.C. 154(b) by 962 days.

(21) Appl. No.: 17/044,819

(22) PCT Filed: Apr. 3, 2019

(86) PCT No.: PCT/EP2019/058403
§ 371 (c)(1),
(2) Date: Oct. 1, 2020

(87) PCT Pub. No.: WO2019/193051
PCT Pub. Date: Oct. 10, 2019

(65) Prior Publication Data
US 2021/0093185 A1     Apr. 1, 2021

(30) Foreign Application Priority Data
Apr. 4, 2018 (GB) ..................... 1805561

(51) Int. Cl.
*A61B 3/10* (2006.01)
*A61B 3/00* (2006.01)
*A61B 3/107* (2006.01)

(52) U.S. Cl.
CPC ............ *A61B 3/101* (2013.01); *A61B 3/0008* (2013.01); *A61B 3/107* (2013.01)

(58) Field of Classification Search
CPC ....... A61B 3/101; A61B 3/0008; A61B 3/107; A61B 3/1015; A61B 1/00002;
(Continued)

(56) References Cited

U.S. PATENT DOCUMENTS 4,169,664 A * 10/1979 Bailey, Jr. .............. A61B 3/112
                                                                606/4
4,917,485 A    4/1990 Baldwin, Sr.
(Continued)

FOREIGN PATENT DOCUMENTS

CN    1678235 A    10/2005
EP    0317768 A1    5/1989
(Continued)

OTHER PUBLICATIONS

Indian Patent Office Action received in Application No. 202017042749, dated Aug. 3, 2022, with English translation, 6 pages.
(Continued)

*Primary Examiner* — Travis S Fissel
(74) *Attorney, Agent, or Firm* — Alliance IP, LLC

(57) ABSTRACT

The present invention provides an ophthalmic device comprising at least one linear array of a plurality of light sources. The linear array is rotationally mounted about a central axis on a mounting body which may contain a motor. The linear array has an inner end and an outer end, and the inner end is mounted closer to the central axis and the mounting body than the outer end. As the array is rotated, it forms a series of concentric and conical rings of light that can be projected onto an eye.

20 Claims, 3 Drawing Sheets

(58) Field of Classification Search
CPC ............ A61B 1/00039; A61B 1/00045; A61B 1/00066; A61B 1/00163; A61B 1/06; A61B 1/0661; A61B 1/227; A61B 1/233; A61B 1/0008; A61B 1/0016; A61B 1/0083; A61B 1/0075; A61B 1/0091; A61B 1/12; A61B 1/13; A61B 1/1208; A61B 1/14
USPC ...... 351/206; 348/77–48; 600/184–185, 188, 600/199–200, 227–228, 235–236, 600/245–246, 109, 112, 122
See application file for complete search history.

(56) References Cited

U.S. PATENT DOCUMENTS

| | | | | |
|---|---|---|---|---|
| 5,416,539 | A * | 5/1995 | Gersten | A61B 3/145 351/212 |
| 5,781,274 | A * | 7/1998 | Moreno | A61B 3/09 351/203 |
| 2009/0161090 | A1* | 6/2009 | Campbell | G01B 11/25 351/212 |
| 2009/0237208 | A1* | 9/2009 | Tsukahara | A61B 5/117 340/5.82 |
| 2014/0148737 | A1* | 5/2014 | Homer | A61H 23/00 606/4 |
| 2015/0138505 | A1 | 5/2015 | Grenon et al. | |
| 2016/0198946 | A1 | 7/2016 | Zhou | |
| 2018/0161595 | A1* | 6/2018 | Fuentes | A61N 5/1049 |

FOREIGN PATENT DOCUMENTS

| | | |
|---|---|---|
| EP | 3332755 A1 | 6/2018 |
| JP | S62290435 A | 12/1987 |
| JP | 2018501936 A | 1/2018 |

OTHER PUBLICATIONS

Japanese Office Action received in Application No. 2021-503205, dated Feb. 14, 2023, with Machine English translation, 8 pages.
PCT International Search Report and W.ritten Opinion in PCT International Application Serial No. PCT/EP2019/058403 mailed on Jun. 12, 2019 (9 pages).
United Kingdom Intellectual Property Office Search Report in GB Patent Application Serial No. GB1805561.6 mailed on Sep. 21, 2019 (3 pages).
KIPO; Office Action issued in Korean Patent Application No. KR 10-2020-7030323, dated Mar. 26, 2024; 9 pages.
SIPO; First Office Action issued in Chinese Patent Application No. CN201980023031.X, dated Jan. 9, 2024; 8 pages.

* cited by examiner

OPHTHALMIC DEVICE

CROSS-REFERENCE TO RELATED APPLICATIONS

This Application is a national stage application under 35 U.S.C. § 371 of PCT International Application Serial No. PCT/EP2019/058403 filed on Apr. 3, 2019 and entitled OPHTHALMIC DEVICE, which application claims the benefit of priority to GB Patent Application Serial No. 1805561.3 filed on Apr. 4, 2018. The disclosures of the prior applications are considered part of and are hereby incorporated by reference in their entirety in the disclosure of this application.

FIELD OF THE INVENTION

The present invention relates to an ophthalmic device for inspection of a patient's eye. In particular, the present invention relates to an ophthalmic device for measuring/observing the cornea surface and the tear/lipid layer. The present invention also relates to a kit of components for an ophthalmic device.

BACKGROUND

Measuring the shape of the anterior surface of the cornea (e.g. to assess astigmatism) is typically carried out using a keratometer which projects a series of black and white concentric rings onto the cornea by back-lighting a placido disc. The reflection of the rings is observed by an ophthalmologist through a hole at the centre of the disc although more recent developments have seen the transfer of the image to a computer for analysis.

A keratometer can also be used to assess non-invasive tear film break-up by observing the distortion or break-up of the reflected ring image. Rapid distortion or breakup can be used to diagnose dry eye.

A number of keratometers and tear scopes are known such as the Keeler Tearscope™ and the commercially available Oculus™ Keratograph and Easy Tear View™ (which superseded the Keeler Tearscope™ and works on the same principles).

The Keeler Tearscope™ was a hand-held device comprising a hemispherical cup mounted on a handle and back-lit by a cold cathode ring light source. The surface of the cup was marked with a grid pattern which is projected onto the patient's eye. The Tearscope™ was held as close to the surface of the eye as possible so that the area illuminated could be maximised. This was often uncomfortable for the patient. The eye was then observed through an observation hole at the centre of the hemispherical cup.

The Oculus™ Keratograph is a desk mounted device having a larger hemispherical cup marked with black concentric rings back lit by a white light source. The patient rests their chin on a chip strap of a head support and the concentric rings are reflected from the patient's eye and observed by a camera mounted at the centre of the hemispherical cup. The back lighting of the concentric rings is very bright to compensate for the spacing of the patient's head from the marked hemispherical cup. This brightness can be uncomfortable for the patient. Furthermore, the hemispherical cup has to be made large (hence the requirement for desk mounting) in order to ensure a large area of the cornea is illuminated due to the spacing between the hemispherical cup and the eye.

Aspects and embodiments of the invention were devised with the foregoing in mind.

SUMMARY OF THE INVENTION

In a first aspect, there is provided an ophthalmic device, said device comprising at least one linear array of a plurality of light sources, the linear array being rotationally mounted about a central axis on a mounting body, the linear array having an inner end and an outer end, wherein the inner end is mounted closer to the central axis and the mounting body than the outer end.

By providing a rotationally mounted linear array of light sources that are angled away from the central axis of rotation, the linear array can be rotated such that each of the plurality of light sources traces a circular path leading to a plurality of concentric (conical) rings of light that can be projected onto a patient's eye. The inventor has found that creating rings of light (rather than back-lighting a surface having blacked-out grids/rings) results in improved contrast between the dark and light reflections on the surface of the eye with a lower brightness of light required. Furthermore, the light sources can be positioned closer to the eye than the diffuse back-lighting sources used in the prior art and this proximity further reduces the brightness needed for effective projection onto the eye. Yet furthermore, providing a plurality of light sources (rather than a single back light) allows tailoring of the rings of light to effect different measuring techniques as discussed below.

The at least one linear array may be provided on a rotatable support. The rotatable support may comprise a linear blade and/or a frustoconical support. The smaller diameter end of the frustoconical support is mounted on the e.g. releasably mounted on the mounting body. It may be secured to the mounting body using a magnetic connection i.e. frustoconical support may have a magnetic surface which is attracted to and held by an opposing magnetic surface of the mounting body.

The or each linear array may form an angle of between 15 and 90 degrees relative to the central rotational axis. Accordingly, the linear blade and/or the frustoconical walls of the frustoconical support may form an angle of between 15 and 90 degrees relative to the central rotational axis.

The larger the angle, the better the projection onto the eye. At smaller angles, the projected ring density will be greater but merging of rings may occur—this can be addressed by switching off some of the LEDs in the or each array as discussed below.

In some embodiments, the or each array may form and angle of around 60 degrees relative to the central rotational axis. Accordingly, the linear blade and/or the frustoconical walls of the frustoconical support may form an angle of around 60 degrees relative to the central rotational axis.

In some embodiments, the angle of the linear array relative to the central axis may be variable (by varying the spacing between the outer end of the linear array and the central axis).

For example, the angle of the linear blade relative to the central axis may be adjustable. In other embodiments, the angle of the walls of the frustoconical support may be adjustable.

The device may comprise a second support interchangeable with the support wherein the angle of the linear array on the second support (relative to the central axis) is different to the angle of the linear array on the support (relative to the central axis).

For example, a frustoconical support having walls forming 60 degrees with the central rotational axis may be interchangeable with a second frustoconical support having walls forming a different angle e.g. greater than 60 degrees with the rotational axis (e.g. up to 90 degrees) or less than 60 degrees with the rotational axis e.g. down to 15 degrees).

This allows a variation in the size and spacing of the rings of light that can be generated with larger rings being useful for adults and smaller rings being useful for children (or those with smaller eye dimensions). This helps maximise corneal coverage of the projection and thus maximise the number of data collection points.

In some embodiments, there are two or more linear arrays each comprising a plurality of light sources. The two linear arrays are preferably equally spaced around the central axis e.g. there may be two arrays spaced from one another by 180 degrees. Each array may be provided on a respective rotational support e.g. linear blade and/or they may be provided equally spaced about the frustoconical support.

In some embodiments at least one of the plurality of light sources and preferably all light sources, is/are LED light sources.

Each light source may be independently selected from white LEDs, blue LEDs, red LEDs, green LEDs or Infra-Red LEDs. In this way, the colour of the rings can be varied. In some embodiments the plurality of light sources in a first linear array may be one colour and a plurality of light sources in a second linear array may be a second colour. For example, the light sources in one of the two linear arrays may be infrared LEDs whilst the other may be white or coloured (e.g. blue LEDs).

In some embodiments, the light sources in the or one of the linear arrays are multi-coloured. This can help to easily identify point of distortion and hence tear film break up. Furthermore, the projection of different coloured rings can help prevent confusion from cross-over in highly aberrated eyes. Blue LEDs can be used for fluorescein viewing. Infra-red LEDs can be used for refractive error measurement.

Each light source may be independently controllable e.g. each may be independently illuminated/independently switched on and off. In this way, each light source and therefore each ring generated by rotation of the light sources can be independently lit so that the pattern for reflection can be tailored e.g. for eye colour. For example, a dense ring pattern (with all or most light sources illuminated) is less easily observed on lighter coloured (e.g. blue/green) eyes owing to the strong scattering. By using a less dense ring pattern (by illuminating only some of the light sources, e.g. only alternate light sources), scattering is reduced. Prior art devices do not allow tailoring of the density ring pattern.

The individual control of the light sources also allows individual light sources to be flashed on and off at different points during rotation allowing projection of customised patterns that can be used for visual field testing wherein peripheral vision is tested.

Each light source may be have an independently controllable intensity. In this way, the brightness of the rings generated through rotation of the linear array can be tailored e.g. for patient sensitivity and/or daylight conditions.

The device may further comprise a frustoconical frame mounted (e.g. releasably mounted) on the mounting body and surrounding the linear array e.g. surrounding the rotatable support (e.g. linear blade and/or the frustoconical support). The frame may be solid or fenestrated. The frame is provided to protect the patient and ophthalmologist from the rotating support. The larger diameter end of the frustoconical frame can form a brow rest for contact with the patient's brow during use. The smaller diameter end is mounted on the mounting body.

The frame may be interchangeable with a second frame, the second frame having struts/walls forming a greater or lesser angle with the rotational axis. In this way, arrays/supports having variations in the angle they form with the central axis can be used as described above.

The support (e.g. linear blade and/or frustoconical support) and/or frame may be releasably mounted on the mounting body. The support/frame may be mountable using a respective magnetic connection i.e. the support/frame may have a respective magnetic end surface which is attracted to and held by an opposing magnetic surface of the mounting body.

The mounting body may house a motor for driving rotation of the linear array/support. The motor may comprise a commutator to connect power and data signals to the rotating array(s) of light sources.

The mounting body may have a through channel aligned with the central rotational axis, with the inner end of the linear array proximal the through channel. This allows a view through the mounting body along the rotational axis.

The mounting body may be mounted (e.g. releasably mounted) on a handle such that the device is a portable, hand-held device. The mounting body may be mountable to the handle using a magnetic connection i.e. the handle may have a magnetic surface which is attracted to and held by an opposing magnetic surface of the mounting body.

The handle may have a hollow chamber for housing a power source e.g. a battery pack (such as a rechargeable battery pack). Additionally/alternatively, the handle may comprise a connection for connection to a power source, e.g. for connection to the power source of a slit lamp or directly to a wall socket.

The device may further comprise an attachment clip for securing a visualisation and/or recording device (e.g. a focussing lens, magnifier, camera or other image recording device such as a mobile phone/smart phone) against the mounting body on the opposing side of the mounting body to the linear array.

The attachment clip may be provided (e.g. releasably provided) on the mounting body and/or on the handle.

The device may further comprise a focussing lens connected (e.g. releasably connected) in alignment with the through channel on the mounting body. The lens may be secured to the mounting body using a magnetic connection i.e. the lens may be mounted in a lens mount having a magnetic surface which is attracted to and held by an opposing magnetic surface of the mounting body.

The device may further comprise a magnifier connected (e.g. releasably connected) in alignment with the through channel on the mounting body. The magnifier may be additionally or alternatively secured to the mounting body using a magnetic connection i.e. the magnifier may be mounted in a magnifier mount having a magnetic surface which is attracted to and held by an opposing magnetic surface of the mounting body.

The device may further comprise a camera connected (e.g. releasably connected) in alignment with the through channel on the mounting body. The camera may be additionally or alternatively secured to the mounting body using a magnetic connection i.e. the camera may be mounted in a camera mount having a magnetic surface which is attracted to and held by an opposing magnetic surface of the mounting body.

The camera may be connectable to data processing and storage means (e.g. in a smart phone or tablet) for storing and processing patient data locally.

The device may further comprise one or more coloured filters connected (e.g. releasably connected) in alignment with the through channel on the mounting body. The filter(s) may be additionally or alternatively secured to the mounting body using a magnetic connection i.e. the filter(s) may be mounted in a filter mount having a magnetic surface which is attracted to and held by an opposing magnetic surface of the mounting body. The filter(s) will facilitate observation of various dyes instilled into the eye. As will be appreciated from the description above, the device is formed of a number of modular components i.e. the mounting body, support, frame, and handle along with the various visualisation devices which are releasably connectable to one another. These modular components can be assembled for use and disassembled for storage/transport. The magnetic connections described above between the components allow for quick and easy assembly and disassembly.

In a second aspect, there is provided a kit comprising:
at least one linear array of a plurality of light sources, and
a mounting body, the linear array being rotationally mountable on the mounting body about a central axis, the linear array having an inner end and outer end, wherein the inner end is mountable closer to the mounting body and central axis than the outer end.

The at least one linear array of a plurality of light sources may be as described above for the first aspect.

The at least one linear array may be provided on a rotatable support as described above for the first aspect.

The kit may comprise a plurality of frustoconical supports, each having a different angle formed by the frustoconical support walls. In other embodiments, the kit may comprise a single frustoconical support with walls that are adjustable to from different angles with the central rotational axis.

The or each frustoconical support may be connectable to the mounting body using a magnetic connection i.e. the support may have a magnetic end surface which is attracted to and held by an opposing magnetic surface of the mounting body.

The kit may further comprise a frustoconical frame mountable on the mounting body for enclosing the linear array e.g. enclosing the support (e.g. linear blade and/or the frustoconical support).

The kit may comprise a plurality of frustoconical frames, each having a different angle formed by the frustoconical frame walls/struts.

The or each frustoconical frame may be connectable to the mounting body using a magnetic connection i.e. the frame may have a magnetic end surface which is attracted to and held by an opposing magnetic surface of the mounting body.

The mounting body may be as described above for the first aspect.

The kit may further comprise a handle on which the mounting body is mountable. The handle may be as described for the first aspect.

The kit may further comprise a focussing lens as described above for the first aspect.

The kit may further comprise a magnifier as described above for the first aspect.

The kit may further comprise a camera as described above for the first aspect.

The kit may further comprise one or more filter(s) as described above for the first aspect.

The camera may be connectable to data processing and storage means (e.g. in a smart phone or tablet) for storing and processing patient data locally.

The invention includes the combination of the aspects and preferred features described except where such a combination is clearly impermissible or expressly avoided.

SUMMARY OF THE FIGURES

So that the invention may be more readily understood, and so that further features thereof may be appreciated, embodiments and experiments illustrating the principles of the invention will now be described by way of example with reference to the accompanying figures in which.

DETAILED DESCRIPTION OF THE INVENTION

Figure 2:
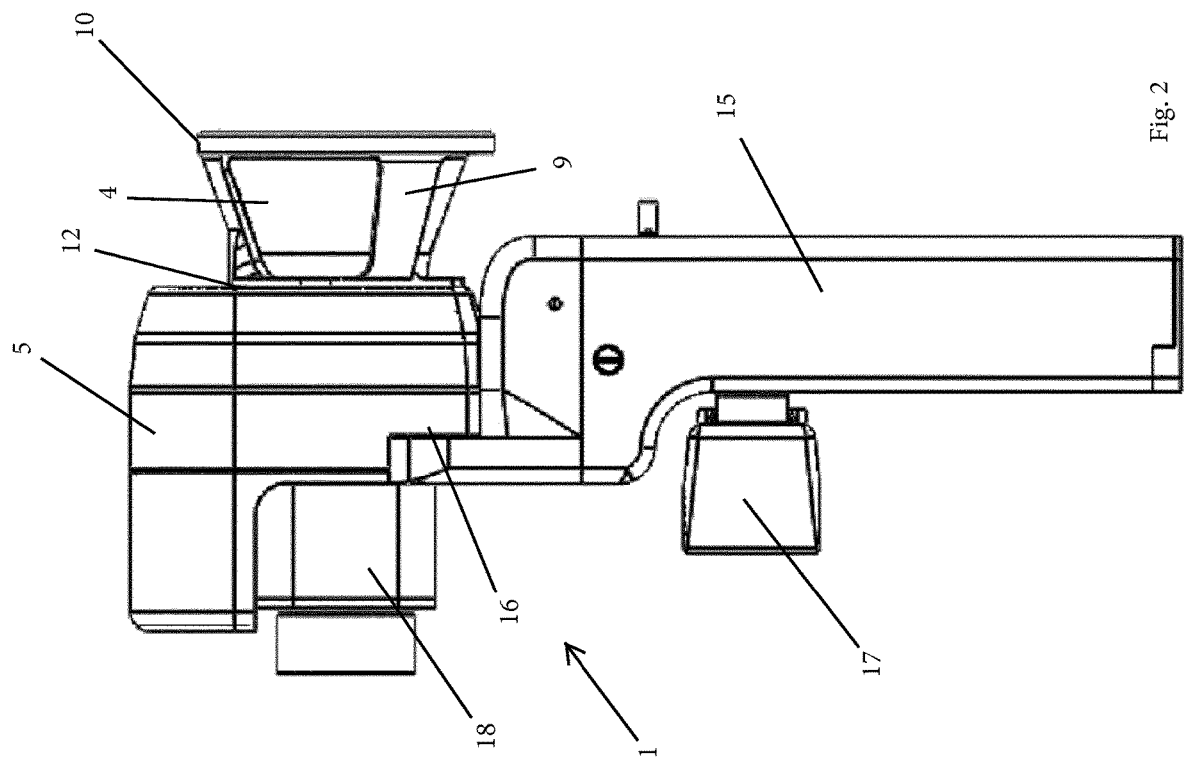
FIG. 2 shows a side view of the first embodiment with a magnifier attached.
Figure 1:
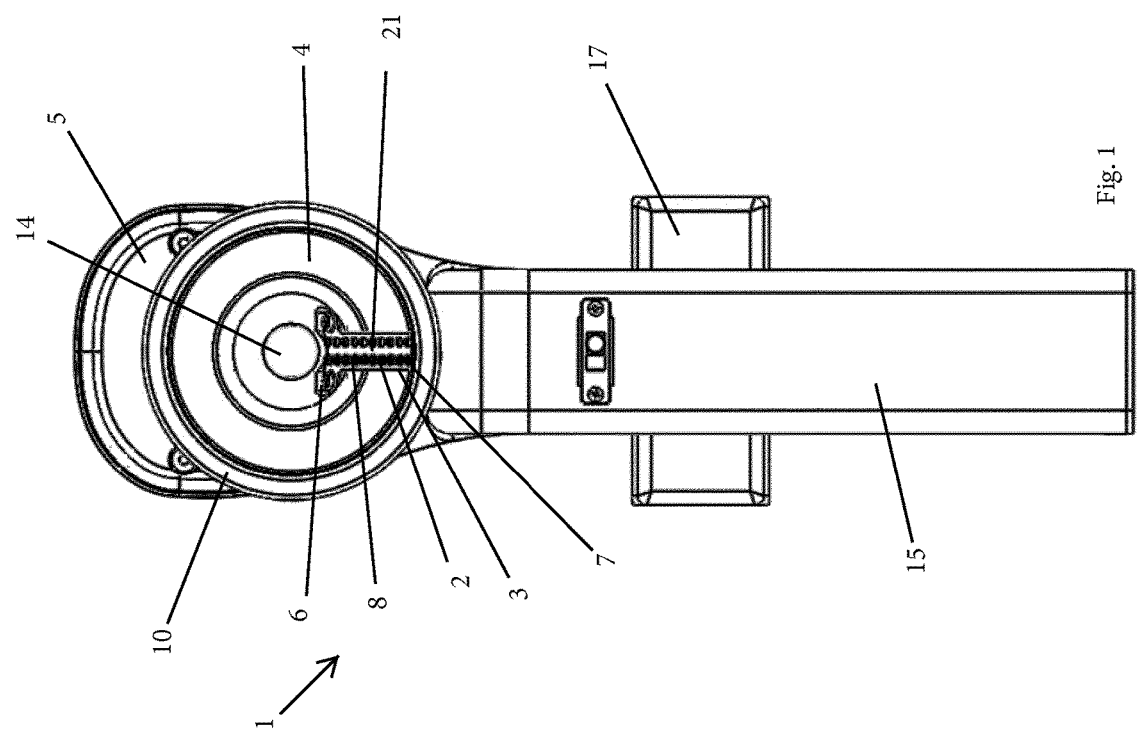
FIG. 1 shows a front view of a first embodiment of the device.

FIGS. 1 and 2 show front and side views respectively of a first embodiment of an ophthalmic device 1.

The device 1 comprises a linear array 2 of light sources 8 mounted on a linear blade support 3 which is itself mounted on a frustoconical support 4. A row of resistors 21 is provided adjacent the linear array 2 of light sources 8 although this could be mounted out of view in other embodiments.

The linear blade 3 and frustoconical support 4 are rotationally mounted about a central rotational axis on a mounting body 5 with the inner end 6 of the linear array 2 being closer to the central axis and the mounting body 5 than the outer end 7.

The smaller diameter end of the frustoconical support 4 is releasably mounted on the mounting body by a magnetic connection. It is received in a circular recess 11 in the mounting body 5.

The mounting body 5 has a through channel 14 aligned with the central rotational axis, with the inner ends 6, 6' of the linear array 2 proximal the through channel. The mounting body 5 houses a motor (not shown) for driving the rotation of the linear array 2 linear blade 3 and support 4.

The device 1 further comprises a fenestrated frustoconical frame 9 mounted on the mounting body 5 (at its smaller diameter end) and surrounding the frustoconical support 4. The frame 9 is provided to protect the patient and ophthalmologist from the rotating support 4. The larger diameter end 10 of the frustoconical frame 9 can form a brow/cheek rest for contact with the patient's brow/cheek during use.

Figure 3:
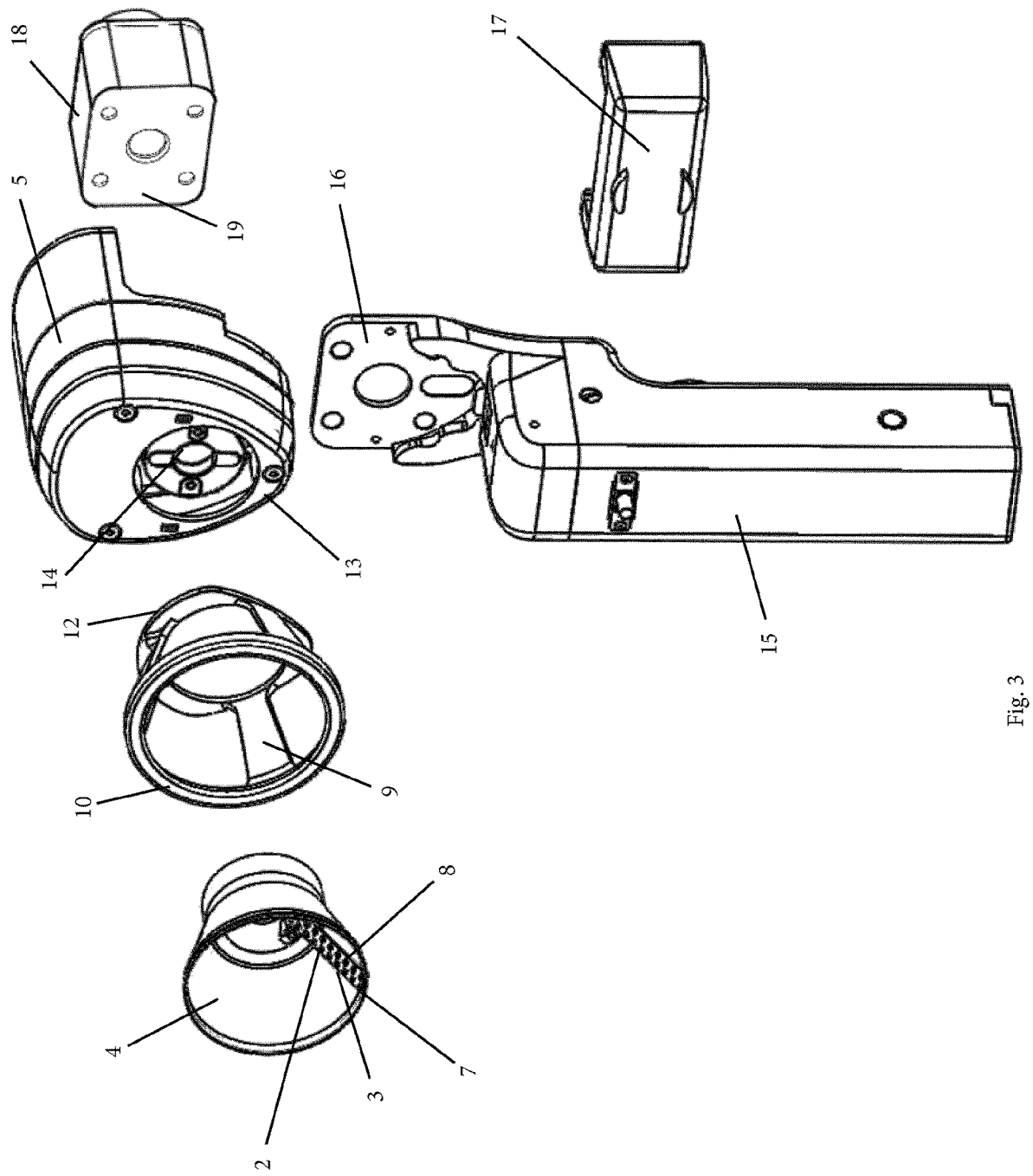
FIG. 3 shows an exploded isometric view of the first embodiment with a magnifier.

The frame 9 is releasably mounted on the mounting body. It comprises an end surface wall 12 (shown in FIG. 3) which is magnetic and which abuts and is held against an opposing magnetic wall 13 on the mounting body 5.

The linear array 2 linear blade 3 and walls of the frustoconical support 4 are at an angle of 60° with respect to the central axis.

The mounting body 5 is releasably mounted on a handle 15 such that the device 1 is a portable, hand-held device. The mounting body 5 is mountable to the handle using a magnetic connection—the handle has a magnetic surface 16 which is attracted to and held by an opposing magnetic surface of the mounting body 5.

The handle 15 has a hollow chamber for housing a power source e.g. a battery pack (such as a rechargeable battery pack) for powering the motor. In other embodiments (not shown) the handle 15 has a connection for connection to a power source, e.g. for connection to the power source of a slit lamp or to a wall socket.

The linear array 2 comprises a plurality of plurality of light sources 8 which are white LEDs.

Each of the plurality of light sources 8 is independently controllable i.e. each can be switched on an off independently and each has an independently controllable intensity.

In use, at least some of the plurality of light sources 8 are illuminated and the motor within the mounting body 5 is used to drive the rotation of the linear array 2 such that each of the illuminated light sources traces a circular path. This leads to a generation of a series of concentric and conical rings of light by means of a persistence of vision effect.

The patient can rest their brow on the large diameter end 10 of the frustoconical frame 9 so that the rings of light are projected onto the patient's eye.

The topography of the cornea and/or the tear film break down can be assessed by monitoring the distortion and/or breakdown of the projected rings.

To facilitate such monitoring, the device may be provided with a visualisation and/or recording device. In the embodiment shown in FIGS. 2 and 3, the device 1 further comprises a magnifier 18 releasably connected to the mounting body 5 in alignment with the through channel 14. The magnifier 18 is secured to the mounting body 5 using a magnetic connection i.e. the magnifier 18 is mounted in a magnifier mount having a magnetic surface 19 which is attracted to and held by an opposing magnetic surface of the mounting body 5.

The projected rings on the eye can be visually observed through the magnifier and any distortion and/or the time for break-up of the rings can be recorded.

Figure 5:
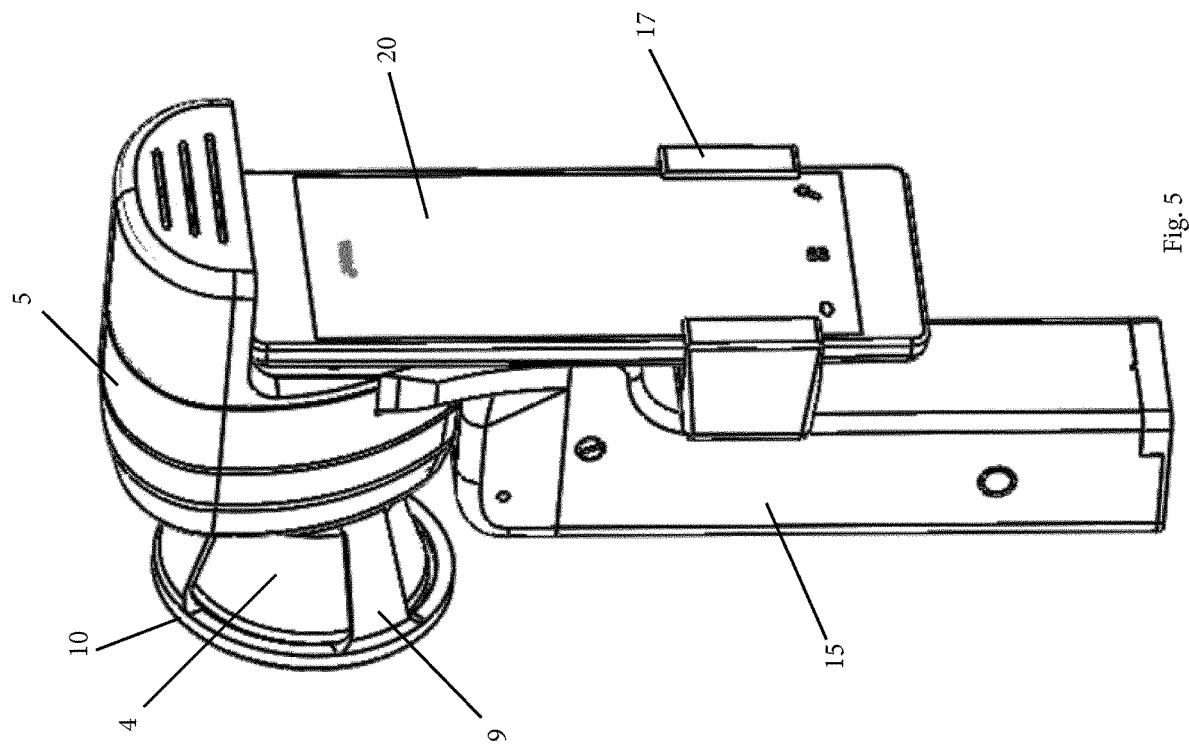
FIGS. 4 and 5 show a side and perspective view of the first embodiment with a smartphone attached.
Figure 4:
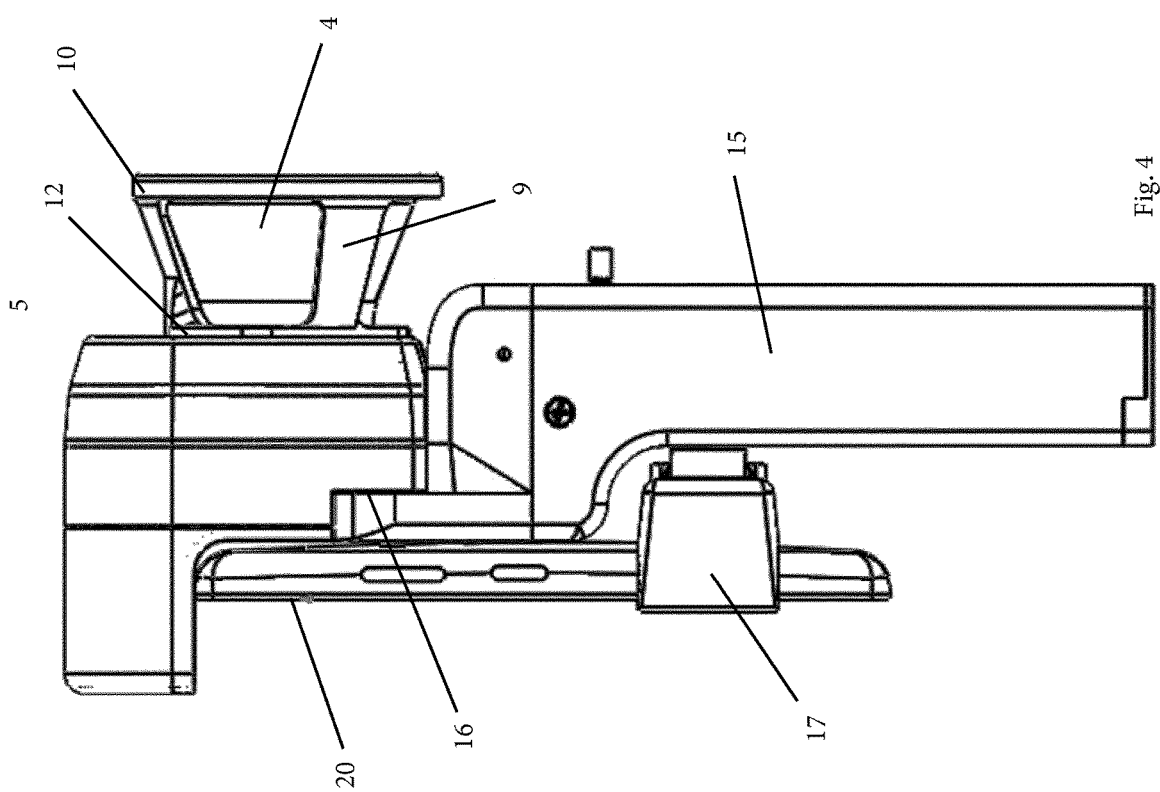

The device 1 further comprises attachment clip 17 provided on the handle 15 for securing a smartphone 20 against the mounting body 5 on the opposing side of the mounting body 5 to the linear array 2. As shown in FIGS. 4 and 5, the smart phone 20 is held so that the smartphone camera is aligned with the through channel 14 so that the projected rings can be recorded.

In order to allow use of the device with patients with both large eye dimensions e.g. adult males, and smaller eye dimensions, e.g. children, the device is provided as a kit with a second support interchangeable with the support wherein the angle of linear array on the second support (relative to the central axis) is different to the angle of the linear array on the support (relative to the central axis).

As will be appreciated from the description above, the device is formed of a number of modular components i.e. the mounting body 5, support 4, frame 9, and handle 15 along with the various visualisation devices which are releasably connectable to one another. These modular components can be assembled for use and disassembled for storage/transport. The magnetic connections described above between the components allow for quick and easy assembly and disassembly.

The device can be used for general anterior eye assessment. This could include detection of scratches on the cornea, scleral redness, pupil reaction time and tear meniscus height. The device can be used for tracking patient symptom history.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the scope of the invention.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

The invention claimed is:

1. An ophthalmic device comprising at least one linear array of a plurality of light sources, the linear array being rotationally mounted about a central axis on a mounting body and being angled away from the central axis of rotation, wherein the linear array can be rotated such that each of the plurality of light sources traces a circular path leading to a plurality of concentric rings of light that can be projected onto a patient's eye, the linear array having an inner end and an outer end, wherein the inner end is mounted closer to the central axis and the mounting body than the outer end and wherein the linear array, when rotated, causes a plurality of concentric rings of light to be projected onto a patient's eye by a persistence of vision effect.

2. The device according to claim 1 wherein the at least one linear array is provided on a rotatable support.

3. The device according to claim 2 wherein the support comprises a linear blade and/or a frustoconical support.

4. The device according to claim 3 wherein the angle of the linear array away from the central axis is adjustable.

5. The device according to claim 2 further comprising a second support interchangeable with the rotatable support and wherein the angle of linear array on the second support is different to the angle of the linear array on the rotatable support.

6. The device according to claim 1 comprising two or more linear arrays equally spaced around the central rotation axis.

7. The device according to claim 1 wherein at least one of the plurality of light sources is an LED light source independently selected from white LEDs, blue LEDs, red LEDs, green LEDs or Infra-Red LEDs.

8. The device according to claim 1 wherein each of the plurality of light sources has an independently controllable intensity/brightness.

9. The device according to claim 1 further comprising a frustoconical frame mounted on the mounting body and enclosing the at least one linear array.

10. The device according to claim 9 further comprising a second frame interchangeable with the frame and wherein the angle of frustoconical walls of the second frame is different to the angle of the frustoconical walls of the frame.

11. The device according to claim 1 wherein the mounting body has a through channel aligned with the central rotational axis.

12. The device according to claim 11 further comprising attachment clips for securing a visualisation and/or recording device on the mounting body in alignment with the through channel.

13. A kit for an ophthalmic device comprising:
at least one linear array of a plurality of light sources, and
a mounting body, the linear array being rotationally mountable on the mounting body about a central axis such that the linear array is angled away from the central axis of rotation and can be rotated such that each of the plurality of light sources, when rotated about the central axis, traces a circular path leading to a plurality of concentric rings of light that can be projected onto a patient's eye, the linear array having an inner end and outer end, wherein the inner end is mountable closer to the mounting body and central axis than the outer end and wherein the linear array, when rotated, causes a plurality of concentric rings of light to be projected onto a patient's eye by a persistence of vision effect.

14. The kit according to claim 13 further comprising a rotatable support on which the at least one linear array is supported.

15. The kit according to claim 14 wherein the support comprises a linear blade and/or a frustoconical support.

16. The kit according to claim 15 comprising a plurality of interchangeable supports wherein the angle of linear array on each support is different to the angle of the linear array on each other support.

17. The kit according to claim 13 further comprising a frustoconical frame mounted on the mounting body and enclosing the linear array.

18. The kit according to claim 17 comprising a plurality of interchangeable frames wherein the angle of walls/struts of each support is different to the angle of walls/struts of each other support.

19. The kit according to claim 13 further comprising one or more of a focusing lens, a magnifier, a filter and a camera for releasable connection to the mounting body.

20. The device according to claim 1 wherein the mounting body can continuously rotate to cause the linear array to project the plurality of concentric rings of light onto a patient's eye.

* * * * *